June 3, 1941. B. H. HALEY Plant Pat. 473
PEACH TREE
Filed Oct. 26, 1939
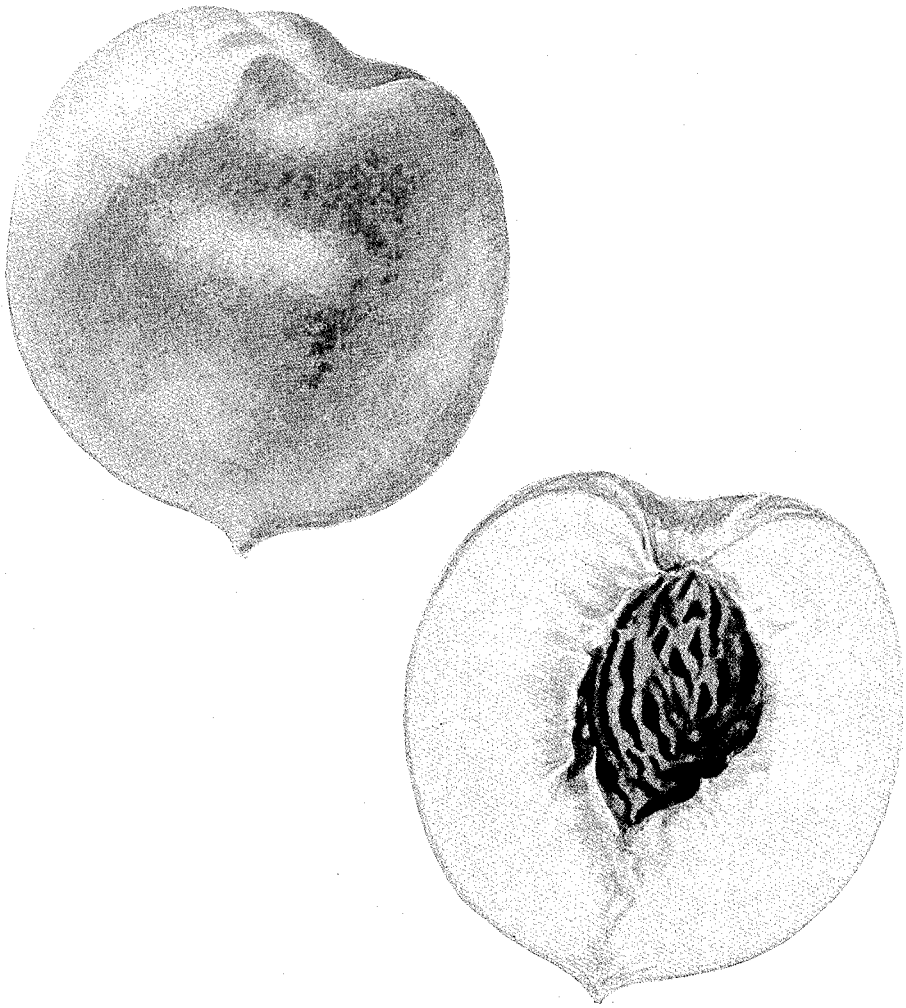
INVENTOR
Benjamin Harrison Haley
By Orville M. Kile
PLANT PATENT AGENT Patented June 3, 1941

UNITED STATES PATENT OFFICE

473

PEACH TREE

Benjamin Harrison Haley, Lakeside, Calif., assignor to Armstrong Nurseries, Inc., Ontario, Calif.

Application October 26, 1939, Serial No. 301,495

1 Claim. (Cl. 47—62)

This new and distinct variety of peach originated some years ago from unknown parentage on property owned by the city of San Diego and located about a mile west of Barrett. From a cook shack located on this property were thrown some peach seeds which sprouted, one of the resulting seedlings being the present new variety. I had occasion to notice this thrifty little seedling which was different from any I had ever before seen. Its vigor and appearance so impressed me that the following year I removed it to my ranch at Lakeside, where its early vigorous habit of growth remains a feature of the original tree and of the trees reproduced from the original.

Two years later the tree fruited and I at once recognized the exceptional quality and the distinctiveness of this fruit as compared with other commonly grown kinds. For several years since that time this tree and trees reproduced from it have consistently borne a heavy crop of excellent fruit each year whereas other similar varieties such as the J. H. Hale and the Elberta have not always borne a crop following our mild southern California winters.

The principal improvement of this peach variety over other similar varieties lies in its much greater vigor and the consistency with which it bears unusually large crops annually. No tests have been made elsewhere and the comparative reaction in other climates is therefore not known, but it is quite evident that the new variety is better adapted to the mild southern California winters than are similar varieties, specifically the J. H. Hale, Elberta, Candoka, and Rio Oso Gem.

The new peach ripens a few days later than the Elberta and the J. H. Hale and a few days earlier than the other varieties above mentioned. The flavor is considered by experts to be superior to that of any of these four popular varieties.

In a general way this peach is similar to the J. H. Hale although its fruit is slightly more elongated in shape and of better quality. As mentioned above, the new variety ripens a few days later than J. H. Hale; it grows more vigorously than that variety, and is much more consistent in producing an unusually large crop each year.

This new peach variety has been asexually reproduced and the resulting trees and their fruits have the same characteristics as the original seedling and its fruits.

The original illustrations accompanying this application show in approximately true colors and slightly enlarged size, a side view and a cross-section view of the fruit of this new peach variety. Following is a detailed description of the new variety. Reference to color plates indicates Ridgway's Color Standards and Nomenclature. Where no reference is indicated, the ordinary dictionary term is intended.

*The tree*

Growth: Very vigorous; productive; spreading, vase form; heavy foliaged; regular and consistent bearer.

Trunk: Medium size and strength; fairly smooth; color between Russet (Plate XV) and Kaiser Brown (Plate XIV), with a silvery overlay.

Branches: Medium size; color reddish-brown, the younger ones being approximately Mahogany Red (Plate II) on the side next the sun, and the older ones between Verona Brown (Plate XXIX) and Angus Brown (Plate III). The side away from the sun is approximately Courge Green (Plate XVII).

*Lenticels.*—Numerous and of medium size.

Leaves:

*Size.*—Average 5½ inches by 1¼ inches. Slightly smaller than leaves of the J. H. Hale.

*Thickness.*—Medium.

*Shape.*—Lanceolate, with acuminate apex. Margin has sharp-pointed serrations.

*Color.*—Between Cerro Green (Plate V) and Cedar Green (Plate VI), on the upper surface. Lower surface approximately Yellowish Oil Green (Plate V).

*Petiole.*—Three-eighths to one-half inch in length.

*Glands.*—Reniform; situated at base of blade; number variable.

*The flower*

Buds:

*Size.*—Medium as compared with most varieties. About the same size as buds of the J. H. Hale and slightly smaller than those of Lukens Honey.

*Length.*—Medium.

*Shape.*—Rounded.

*Color.*—Approximately the same as J. H. Hale and deeper than Lukens Honey.

Blossoms:

*Size.*—About the same as J. H. Hale. Petals measure approximately ⅓ inch wide and ⅖ inch long.

*Color.*—Approximately the same as J. H. Hale.

*Pollen.*—Great quantities of viable pollen are produced. The variety is probably self-fertile although exhaustive tests have not yet been made.

Blooming dates: In southern California blossoms open April 4 to 15 after a warm winter and from March 10 to 20 after a cold winter.

*The fruit*

Maturity: Midseason variety, maturing early August—a few days later than the J. H. Hale. In an average year the season is from August 8 to 20.

Size: Large 2½ to 3¼ inches in cross section. Axial diameter 3 inches; transverse in suture plane 3 inches; at right angles to suture plane about 3¼ inches.

Form: Somewhat elongated; uniform; halves not quite equal but near enough to appear symmetrical; one-half very slightly raised along suture.

*Suture.*—Shallow; distinct, extending from base to slightly beyond the pistil point.

*Ventral surface.*—Slightly rounded.

*Cavity.*—Medium depth, ⅜ to ½ inch.

*Base.*—Slightly oblique.

*Apex.*—Pointed and fairly prominent.

Skin: Of medium thickness; tough; does not crack; adheres to flesh when ripe.

*Pubescence.*—Scant and light in color.

*Color.*—Approximately Light Cadmium (Plate IV), mottled with Light Jasper Red to Pompeian Red (Plate XIII) where exposed to the sunlight.

Flesh:

*Color.*—Between Light Cadmium (Plate IV) and Deep Chrome (Plate III), stained around the pit with Scarlet Red to Carmine (Plate I).

*Texture.*—Fine and firm; fiber moderate; ripens evenly.

*Juice.*—Plentiful and rich.

*Flavor.*—Sweet but with slightly acid taste.

*Aroma.*—Moderate.

*Eating quality.*—Excellent.

Stone: Free, retaining very little fibre; tendency to split is slight.

*Size.*—One and one-half inches long by 1¼ inches wide by ¾ inch thick. Slightly smaller than stone of a comparable J. H. Hale peach.

*Form.*—Oblong; base slightly oblique; sides unequal; apex sharp pointed.

*Surface.*—Irregularly furrowed toward apex; ridged and pitted from near-center to base; ridges interrupted on each side, smooth toward apex; ventral edge thick; dorsal edge narrow with grooves near base and apex.

Shipping qualities: Excellent. Specimens mailed in Ontario, California, on August 15 arrived in Washington, D. C., in excellent condition on the morning of August 17. This quality makes the new variety good for use in distant markets.

Uses: Good as a dessert, culinary, and canning peach.

Having thus disclosed my invention, I claim: A new and distinct variety of peach tree of the general type of the J. H. Hale with qualities in combination substantially as shown and described, characterized particularly by its great vigor; its later ripening date; its consistency in producing an unusually large crop of fruit each year; and its somewhat elongated fruit of pleasing flavor, large size, exceedingly deep yellow color, and excellent shipping qualities.

BENJAMIN H. HALEY.